(12) United States Patent
Ferguson et al.

(10) Patent No.: US 9,198,656 B1
(45) Date of Patent: Dec. 1, 2015

(54) LOCKING SUTURE LOOP APPARATUS SURGERY

(71) Applicant: RIVERPOINT MEDICAL, LLC, Portland, OR (US)

(72) Inventors: Patrick Edward Ferguson, Portland, OR (US); Patrick Joseph Ferguson, Portland, OR (US); Wayne Jay Black, Portland, OR (US)

(73) Assignee: River Point Medical, LLC, Portland, OR (US)

( * ) Notice: Subject to any disclaimer, the term of this patent is extended or adjusted under 35 U.S.C. 154(b) by 0 days.

(21) Appl. No.: 14/706,199

(22) Filed: May 7, 2015

Related U.S. Application Data

(63) Continuation of application No. 14/017,619, filed on Sep. 4, 2013.

(51) Int. Cl.
*A61B 17/06* (2006.01)

(52) U.S. Cl.
CPC ..... *A61B 17/06004* (2013.01); *A61B 17/06066* (2013.01); *A61B 17/06166* (2013.01); *A61B 2017/061* (2013.01); *A61B 2017/0608* (2013.01); *A61B 2017/06052* (2013.01); *A61B 2017/06176* (2013.01)

(58) Field of Classification Search
CPC ....................................... B65H 69/06
USPC ................ 606/228–231; 57/22, 202; 128/898
See application file for complete search history.

(56) References Cited

U.S. PATENT DOCUMENTS

| | | | | |
|---|---|---|---|---|
| 4,950,285 | A * | 8/1990 | Wilk | 606/232 |
| 5,643,295 | A * | 7/1997 | Yoon | 606/151 |
| 5,699,657 | A * | 12/1997 | Paulson | 57/22 |
| 6,296,659 | B1 * | 10/2001 | Foerster | 606/224 |
| 2009/0062851 | A1 * | 3/2009 | Rosenblatt | 606/228 |

* cited by examiner

*Primary Examiner* — Todd Manahan
*Assistant Examiner* — Charles Wei
(74) *Attorney, Agent, or Firm* — Timothy E. Siegel Patent Law, PLLC; Timothy E. Siegel

(57) ABSTRACT

A surgery using a suture assembly made of a continuous length of braided suture material defining an interior lumen, and forming a loop and a tail, and further comprising a first length and a second length, conceptually divided at a midpoint of the loop. The tail includes first, intermediate and second regions. The first region is formed by the first length breaching the second length and entering the interior lumen of the second length, and extending within the second length. The intermediate region is formed by the first length breaching and exiting the second length, so that the first length and the second length extend in adjacent relation. Finally, the third region is formed by the second length breaching the first length and entering the lumen of the first length and extending within the second length. The transitions between the regions of the tail offer resistance to slippage.

11 Claims, 7 Drawing Sheets

Fig. 1A

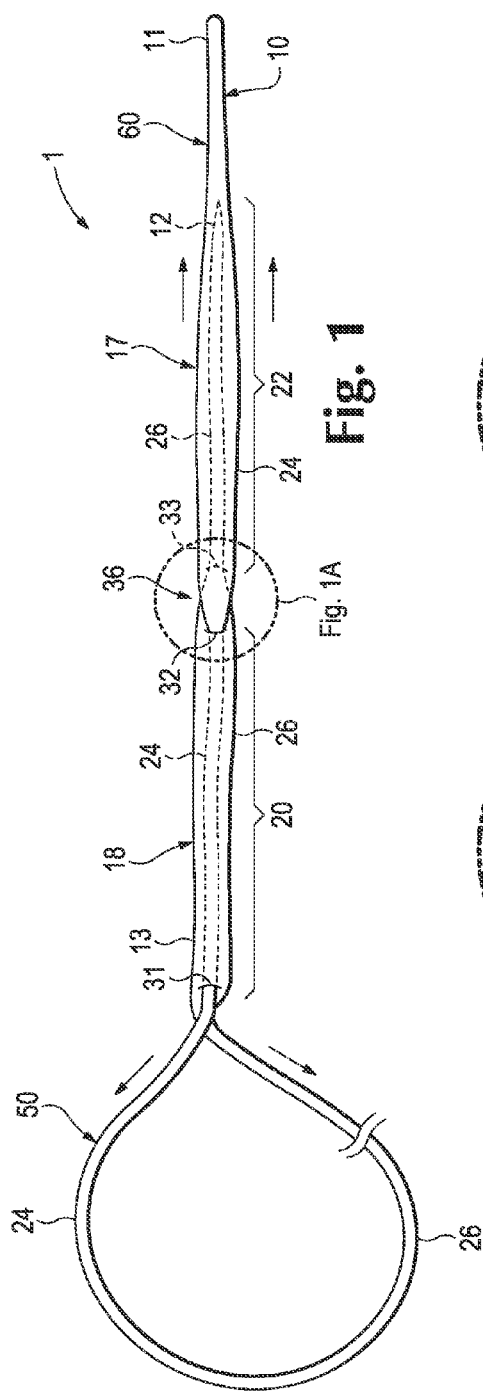

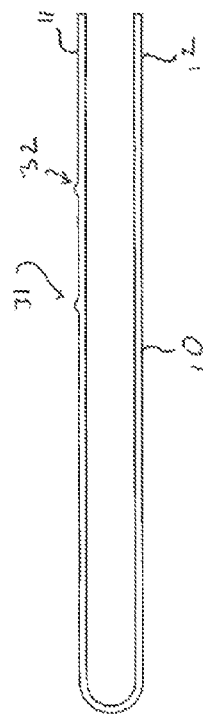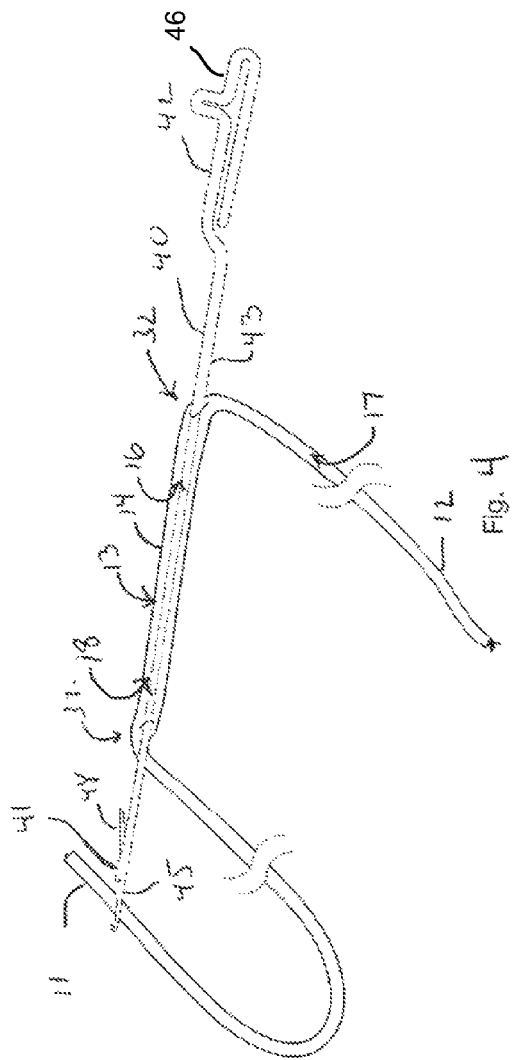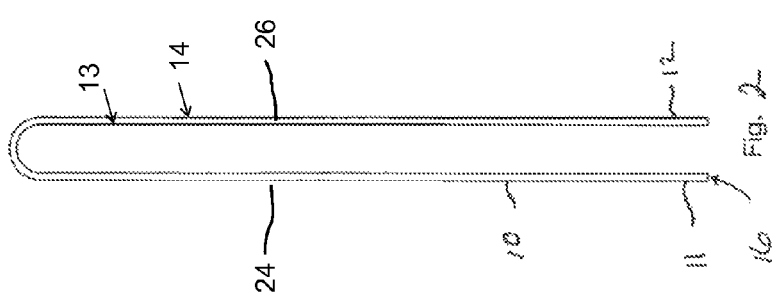

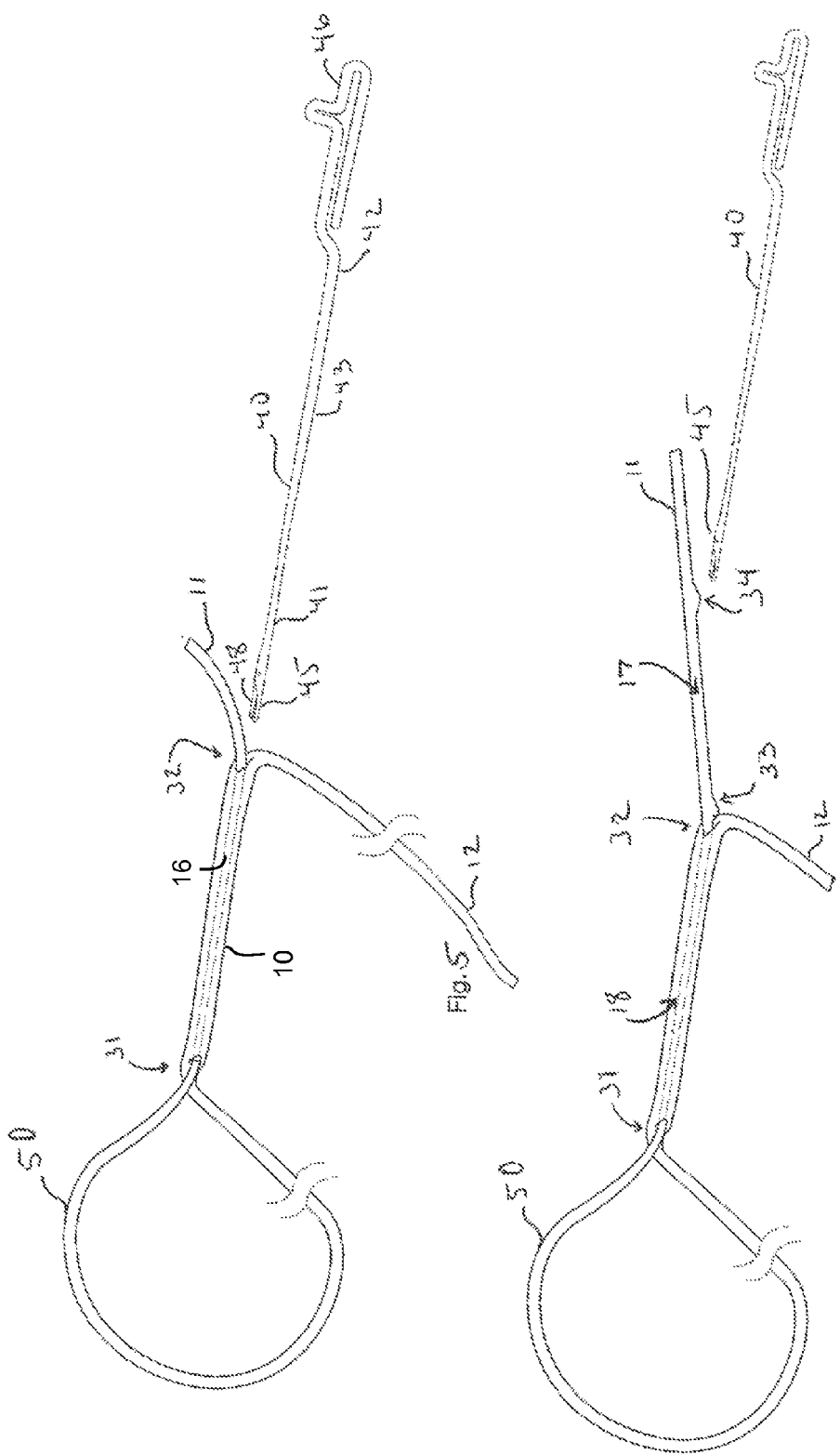

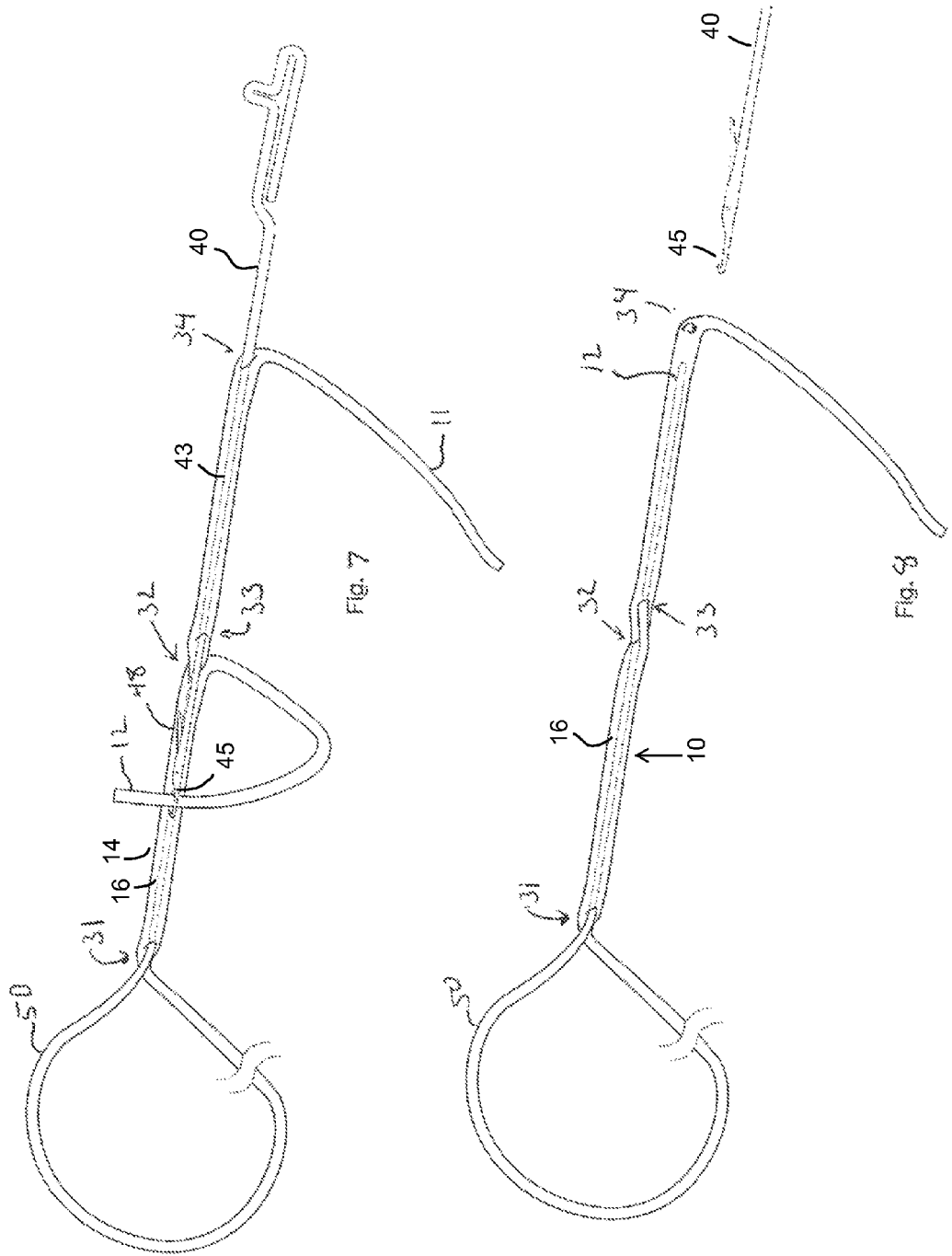

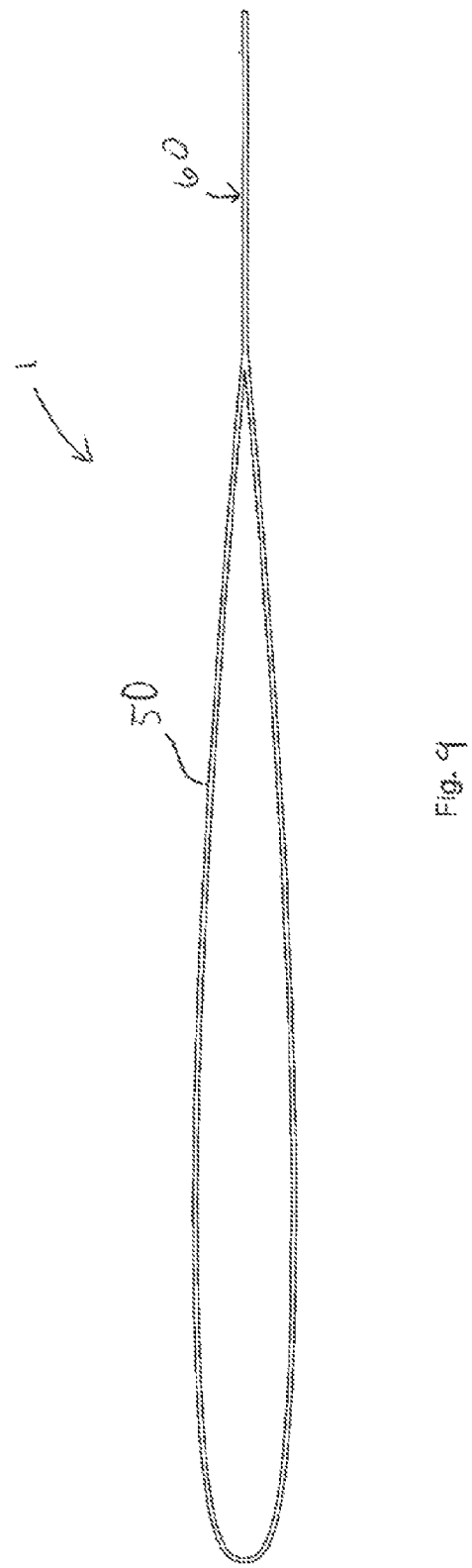

LOCKING SUTURE LOOP APPARATUS SURGERY

RELATED APPLICATIONS

This application is a continuation of application Ser. No. 14/017,619, filed Sep. 4, 2013, which is incorporated herein by reference as if fully set forth herein,

FIELD

This disclosure relates to suture systems and more particularly, to suture loop apparatus and methods for use in surgical techniques.

BACKGROUND

Various surgical techniques require the use of a suture that engages tissue. Suture loops provide a loop at one end and a single tail at the other end. A known suture loop that is constructed from a braided tube suture passes one of the two tails through the lumen defined by the braided tube. Tension on the loop and the outer tail causes the braided tube to reduce in diameter and frictionally engage the inner tail that is disposed within the lumen. In instances where the tension is relieved, there may be slippage between the inner tail and the outer braid, potentially resulting in eventual disengagement.

In view of these and other issues, it would be most desirable to provide an improved suture loop with a positive fixation that does not rely on a constant tension to affect the fixation.

SUMMARY

In a first separate aspect, the present invention may take the form of a suture assembly made of a continuous length of braided suture material defining an interior lumen, and forming a loop and a tail, and further comprising a first length and a second length, conceptually divided at a point on the loop. The tail includes a first region most proximal to the loop, a second region most distal to the loop and an intermediate region joining the first and second regions. The first region of the tail is formed by the first length of suture material, breaching the second length of suture material and entering the interior lumen of the second length of suture material, thereby closing the loop, and extending within the second length of suture material and the intermediate region of the tail is formed by the first length of suture material breaching and exiting the second length of suture material, so that the first length of suture material and the second length of suture material extend in adjacent relation. Finally, the third region of the tail is formed by the second length of suture material breaching the first length of suture material and entering the lumen of the first length of suture material and extending within the second length of suture material. The transitions between the regions of the tail offer resistance to slippage between the first length of suture material and the second length of suture material.

In a second separate aspect, the present invention may take the form of a method of making a suture loop, comprises: providing a length of suture having a suture first end and a suture second end opposite the suture first end, the suture comprises a tubular braid structure comprising strands defining a suture wall having a suture outer surface and a lumen therethrough; defining a first penetration point and a second penetration point a predetermined distance from the first penetration point, the first penetration point and second penetration point are located a predetermined distance from the suture first end and suture second end; disposing the suture first end into the first penetration point, through the lumen and out of the second penetration point forming a loop; defining a third penetration point a predetermined distance from the second penetration point, with the second penetration point between the third penetration point and the first penetration point, and wherein the second penetration point and the third penetration point are adjacent to each other; and disposing the suture second end into the third penetration point and into the lumen, wherein a splice is defined at the second penetration and the third penetration.

BRIEF DESCRIPTION OF THE FIGURES

FIG. 1 shows a side view of a suture loop, in accordance with an embodiment.
FIG. 1A shows a detail view of circle 1A, in FIG. 1.
FIG. 1B shows the detail view of FIG. 1A, rotated 90°.
FIG. 2 shows a side view of suture.
FIG. 3 shows a side view of a suture loop construct, in accordance with an embodiment.
FIG. 4 shows a side view of a suture loop construct, in accordance with an embodiment.
FIG. 5 shows a side view of a suture loop construct, in accordance with an embodiment.
FIG. 6 shows a side view of a suture loop construct, in accordance with an embodiment.
FIG. 7 shows a side view of a suture loop construct, in accordance with an embodiment.
FIG. 8 shows a side view of a suture loop construct, in accordance with an embodiment.
FIG. 9 shows a side view of the suture loop in accordance with the embodiment of FIG. 1.

DETAILED DESCRIPTION

Figure 10:
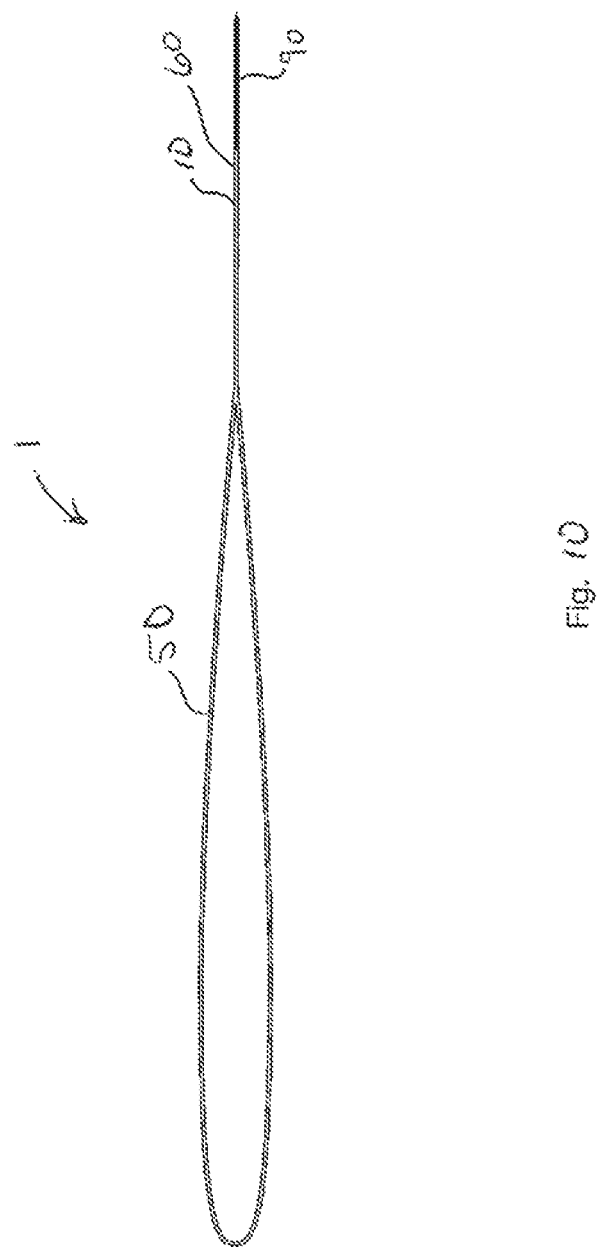
FIG. 10 shows a side view of the needled suture loop, in accordance with an embodiment.

References will now be made to embodiments illustrated in the drawings and specific language which will be used to describe the same. It will nevertheless be understood that no limitation of the scope of the invention is thereby intended, such alterations and further modifications in the illustrated devices, as such further applications of the principles of the invention as illustrated therein as being contemplated as would normally occur to one skilled in the art to which the invention relates.

In accordance with embodiments, a suture loop is provided that is made entirely of braided biocompatible suture material, such as, but not limited to high strength UHMWPE (ultra-high molecular weight polyethylene), polyester, mixtures thereof, and bio-absorbable compounds and mixtures thereof. It is to be understood that any satisfactory material may be used for the suture loop. It is also understood that the suture loop may comprise a mixture of materials, such as a braid comprising strands of UHMWPE and polyester.

In accordance with embodiments, a suture loop is provided that includes a fixed loop size whose fixation is not dependent on maintaining tension on the suture so as to engage an outer braid onto an inner tail. This ensures firm, reliable fixation throughout various physiological conditions, such as, but not limited to, during the healing process and body movement.

FIG. 1 is a side view of an embodiment of a suture assembly 1, comprising a loop 50 and a tail 60. Assembly 1 is made of a continuous length of braided, lumen-defining suture material 10, having a first end 11 and a second end 12. Entirely for ease of description, suture material may be conceptually divided into a first length 24, extending from end 11 to a midpoint of length 10, and a second length 26 extending from end 12 to the midpoint of length 10.

Referring to FIG. 2, there is shown a length of suture 10 having a suture first end 11 and a suture second end 12 opposite the suture first end 11. The suture 10 comprises a tubular braid structure comprising strands defining a suture wall 13 having a suture outer surface 14 and a lumen 16 therethrough, as shown in FIG. 4. The lumen 16 comprises a first end lumen portion 17 at the suture first end 11 and a second lumen portion 18 near too, but displaced from, the suture second end 12.

In the embodiment of FIG. 1, the loop 50 is defined by the entry of first length 24 into second length 26 at penetration point 31. Referring more specifically to FIGS. 1A and 1B, first length 24 extends within lumen 18 of length 26 until it reaches a second penetration point 32, where first length 24 emerges from lumen 18 of second length 26. First length 24 and second length 26 extend in adjacent relation until a third penetration point 33, where second length 26 enters lumen 17 of first length 24. Second length 26 extends within first length 24 until either end 11 or end 12 (as shown in FIG. 1) is reached.

As shown in FIG. 1, a first tail region 20 is defined as that region where the suture first end 11 is within the second end lumen portion 18. A second tail region 22 is defined as that region where the suture second end 12 is within the first end lumen portion 17. The region between the first tail region 20 and the second tail region 22 is defined as a third tail region 36. Relative motion between the suture first end 11 and the suture second end 12 is prevented by the exit of first length 24 from second length 26 at second penetration point 32, and the entry of second length 26 into first length 24 at third penetration point 33. Typically, intermediate region 36 is less than a centimeter in length.

An embodiment of a method of making a suture loop 1 comprises providing a length of suture 10 having a suture first end 11 and a suture second end 12 opposite the suture first end 11. The suture 10 comprises a tubular braid structure comprising strands defining a suture wall 13 having a suture outer surface 14 and a lumen 16 therethrough, as shown in FIG. 2. Defining a first penetration point 31 and a second penetration point 32 a predetermined distance from the first penetration point 31, the first penetration point 31 and second penetration point 32 are located a predetermined distance from the suture first end 11 and suture second end 12, as shown in FIG. 3. Providing a lacing tool 40 comprising an elongated shaft 43 having a shaft first end 41 and a shaft second end 42, a handle 46 optionally formed in the shaft second end 42, the shaft first end 41 formed into a hook 45, the shaft first end 41 further comprising a lever 48 pivotally coupled to the shaft first end 41 adjacent the hook 45 operable to close the hook 45 in a first position and to open the hook 45 in a second position, as shown in FIG. 4. Advancing the hook 45 of the lacing tool 40 from the suture outer surface 14 to the lumen 16 at the second penetration point 32 by advancing the hook 45 through the strands of the braid without breaking the strands. Advancing the hook 45 to the first penetration point 31 within the lumen 16. Advancing the hook 45 from the lumen 16 to the suture outer surface 14 at the first penetration point 31 by advancing the hook 45 through the strands of the braid without breaking the strands, a portion of the shaft 43 extending through the lumen 16 between the second penetration point 32 and the first penetration point 31, as shown in FIG. 4. Placing the suture first end 11 into the hook 45 and closing the lever 48, as shown in FIG. 4. Pulling the hook 45 so as to pull the suture first end 11 into the first penetration point 31, through the lumen 16 and out of the second penetration point 32 forming a loop 50 and removing the lacing tool 40 from the suture 10, as shown in FIG. 5.

The method further comprising defining a third penetration point 33 and a fourth penetration point 34 a predetermined distance from the second penetration point 32, with the second penetration point 32 between the third penetration point 33 and the first penetration point 31, and wherein the second penetration point 32 and the third penetration point 33 are adjacent to each other, as shown in FIG. 6. Advancing the hook 45 of the lacing tool 40 from the suture outer surface 14 to the lumen 16 at the fourth penetration point 34 by advancing the hook 45 through the strands of the braid without breaking the strands. Advancing the hook 45 to the third penetration point 33 within the lumen 16. Advancing the hook 45 from the lumen 16 to the suture outer surface 14 at the third penetration point 33 by advancing the hook 45 through the strands of the braid without breaking the strands, a portion of the shaft 43 extending through the lumen 16 between the fourth penetration point 34 and the third penetration point 33, as shown in FIG. 7. Placing the suture second end 12 into the hook 45 and closing the lever 48, as shown in FIG. 7. And, pulling the hook 45 so as to pull the suture second end 12 into the third penetration point 33, into the lumen 16, wherein a length of the suture second end 12 is predetermined such that the suture second end 12 does not exit the lumen 16 when the lacing tool 40 is withdrawn from the suture 10 at the fourth penetration point 34, as shown in FIG. 8.

FIG. 1 shows the resulting suture loop 1 made in accordance with the embodiment provided above. FIG. 9 shows a side view of the suture loop 1 of the embodiment of FIG. 1.

Figure 11A:
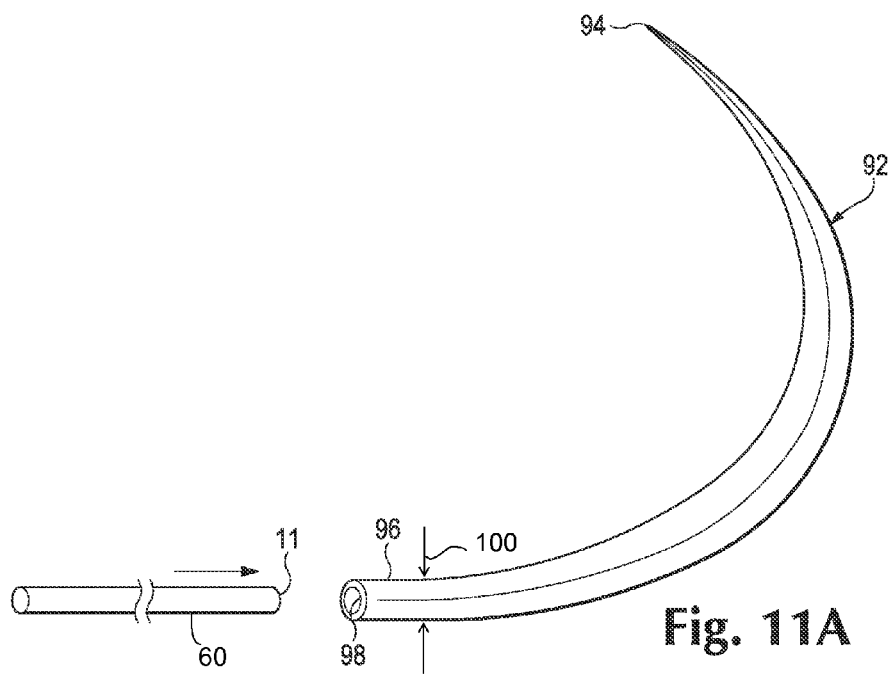
FIG. 11A shows a step in the manufacturing of a suture assembly according to one embodiment of the present invention.
Figure 11B:
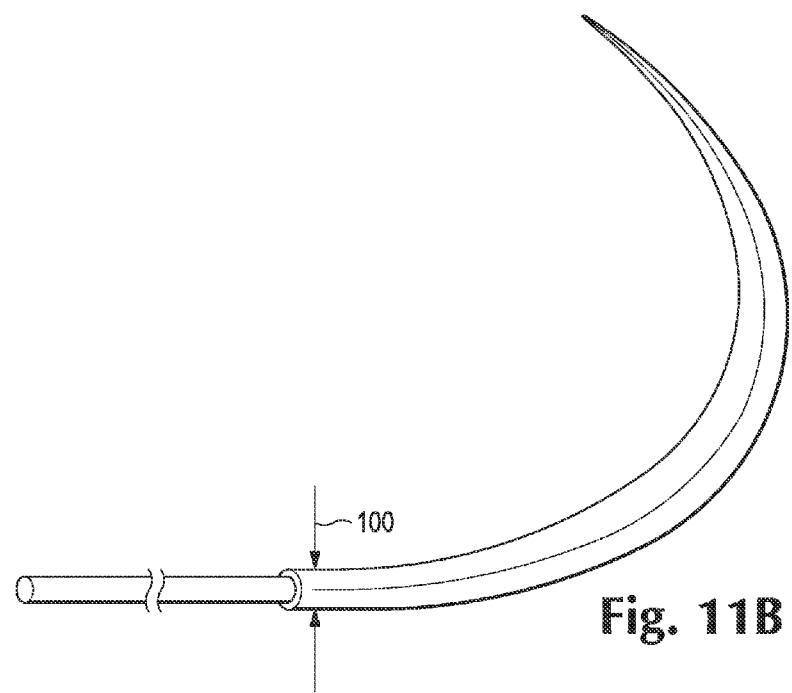
FIG. 11B shows a subsequent and final step in the manufacturing of a suture

FIG. 10 shows a side view of a suture loop 1 wherein a needle 90 is coupled to the tail 60. FIGS. 11A and 11B show steps in the process of manufacturing a suture assembly having a curved needle 92 at the end of the tail 60. In accordance with an embodiment, the end 96 of the needle 92 that is opposite the sharp point 94 forms a hollow tube 98 of malleable metal (a "swage" in industry terminology). The end 11 of tail 60 is inserted into hollow tube 98, to which force 100 is then applied to crimp ("swage," in industry terminology) needle end 96 about end 11 of tail 60.

A method of making a suture loop, in accordance with an embodiment, comprising providing a length of suture having a suture first end and a suture second end opposite the suture first end, the suture comprising a tubular braid structure comprising strands defining a suture wall having a suture outer surface and a lumen therethrough, defining a first penetration point and a second penetration point a predetermined distance from the first penetration point, the first penetration point and second penetration point are located a predetermined distance from the suture first end and suture second end, disposing the suture first end into the first penetration point, through the lumen and out of the second penetration point forming a loop, defining a third penetration point a predetermined distance from the second penetration point, with the second penetration point between the third penetration point and the first penetration point, and wherein the second penetration point and the third penetration point are adjacent to each other; and disposing the suture second end into the third penetration point and into the lumen.

By way of example of the use of embodiments of the suture assembly 1 herein, an anterior cruciate ligament graft may be prepared by arranging loop 50 about the graft, piercing the transverse center of the graft with needle 90, pulling the tail 60 through the graft until loop 50 is taut about the graft, moving the needle laterally along the graft, and repeating the operation, to form a "baseball stitch."

A method for using a suture assembly 1 comprises advancing the needle 90 and tail 60 into and out of two tissue portions, advancing the tail 60 through the loop 50, pulling tension on the tail 60 such that the loop 50 and the tail 60 engage the two tissue portions such that the two tissue portions are drawn together, and tying a knot in the tail 60 to retain the suture loop 50 in engagement with the two tissue portions.

Another method for using a suture assembly 1 comprises advancing the needle 90 into and out of a first tissue portion, advancing the tail 60 through the loop 50, pulling tension on the tail 60 such that the loop 50 and the tail 60 engage the first tissue portion such that the suture loop 50 is anchored to the first tissue portion, advancing the tail 60 through a second tissue portion, pulling tension on the tail 60 such that the tail 60 engages the first tissue portion and the second tissue portion such that the first tissue portion and the second tissue portions are drawn together, and tying a knot in the tail 60 to retain the suture loop 50 in engagement with the first tissue portion and the second tissue portion.

One type of surgery in which tissue portions are engaged together are surgeries reattaching muscle to ligament, from which it has been torn away. For example, repair of the attachment of calf muscle to the Achilles tendon.

While the invention has been described in connection with specific embodiments thereof, it will be understood that it is capable of further modification, and this application is intended to cover any variations, uses, or adaptations of the invention following, in general, the principles of the invention and including such departures from the present disclosure as come within known or customary practice in the art to which the invention pertains and as may be applied to the essential features hereinbefore set forth, and as fall within the scope of the invention and the limits of the appended claims.

The invention claimed is:

1. A method of attaching a length of suture to body tissue, comprising:
   (a) Providing a suture assembly, including:
      i. a continuous length of braided suture material defining an interior lumen, and forming a loop and a tail, and further comprising a first length and a second length, conceptually divided at a point on said loop;
      ii. wherein said tail comprises a first region most proximal to said loop, a second region most distal to said loop and an intermediate region joining said first and second regions;
      iii. said first region of said tail is formed by said first length of suture material, breaching said second length of suture material and entering said interior lumen of said second length of suture material, thereby closing said loop, and extending longitudinally within said second length of suture material;
      iv. said intermediate region of said tail is formed by said first length of suture material breaching and exiting said second length of suture material, at a place longitudinally displaced from where said first length entered said second length, so that said first length of suture material and said second length of suture material extend in adjacent relation;
      v. said third region of said tail is formed by said second length of suture material breaching said first length of suture material and entering said lumen of said first length of suture material and extending within said first length of suture material;
      vi. a needle attached to said third region of said tail; and
      vii. wherein transitions between said regions of said tail offer resistance to slippage between said first length of suture material and said second length of suture material;
   (b) placing said loop about said tissue;
   (c) introducing said tail through the loop, piercing said tissue with said needle and pulling said tail and a first portion of said loop through said tissue, until a second portion of said loop encircles said tissue and is pulled taut.

2. The method of claim 1, wherein said suture material is comprised of ultra-high molecular weight polyethylene.

3. The method of claim 1, wherein said needle is straight.

4. The method of claim 1, wherein said needle is hooked.

5. The method of claim 1, wherein said needle defines a pointed end and a blunt end opposed to said pointed end, and wherein said blunt end defines a tube of malleable material, and wherein said end of said tail is inserted into said tube, which is swaged about it.

6. The method of claim 1, wherein steps (b) and (c) are repeated.

7. The method of claim 6, including the further steps of attaching said tissue to a nearby piece of tissue by, after performing the action of claim 6, performing steps (b) and (c) on said nearby piece of tissue, and thereby pulling said tissue and said nearby tissue into mutual proximity.

8. The method of claim 7, wherein steps (b) and (c) are repeated on said nearby tissue.

9. The method of claim 1, wherein said tissue includes muscle.

10. The method of claim 1, wherein said tissue includes tendon.

11. The method of claim 10, wherein said tendon is an anterior crucifer ligament.

* * * * *